(12) United States Patent
Dayton

(10) Patent No.: US 10,293,066 B2
(45) Date of Patent: May 21, 2019

(54) DECONTAMINATION SYSTEM AND DECONTAMINATION UNIT HOUSING EQUIPPED WITH REMOTE CONTROL

(71) Applicant: Diversey, Inc., Charlotte, NC (US)

(72) Inventor: Roderick M. Dayton, Strongsville, OH (US)

(73) Assignee: Diversey, Inc., Charlotte, NC (US)

( * ) Notice: Subject to any disclaimer, the term of this patent is extended or adjusted under 35 U.S.C. 154(b) by 0 days.

(21) Appl. No.: 15/399,456

(22) Filed: Jan. 5, 2017

(65) Prior Publication Data

US 2017/0112953 A1    Apr. 27, 2017

Related U.S. Application Data

(63) Continuation of application No. PCT/US2016/039506, filed on Jun. 27, 2016.

(60) Provisional application No. 62/184,641, filed on Jun. 25, 2015.

(51) Int. Cl.
| | |
|---|---|
| *F21V 15/00* | (2015.01) |
| *F21V 15/01* | (2006.01) |
| *A61L 2/10* | (2006.01) |
| *G08C 17/02* | (2006.01) |

(52) U.S. Cl.
CPC ............. *A61L 2/10* (2013.01); *F21V 15/01* (2013.01); *G08C 17/02* (2013.01); *F21V 15/00* (2013.01); *G08C 2201/30* (2013.01); *G08C 2201/91* (2013.01)

(58) Field of Classification Search
None
See application file for complete search history.

(56) References Cited

U.S. PATENT DOCUMENTS

| | | |
|---|---|---|
| 5,039,867 A | 8/1991 | Nishihara |
| 6,861,658 B2 | 3/2005 | Fiset |
| 7,198,624 B2 | 4/2007 | Muzzi |
| 7,229,467 B2 | 6/2007 | Spivak |
| 7,476,885 B2 | 1/2009 | Garcia |
| 7,476,888 B2 | 1/2009 | Fiset |
| 7,626,187 B2 | 12/2009 | Younts |

(Continued)

FOREIGN PATENT DOCUMENTS

| | | | |
|---|---|---|---|
| GB | 2198614 A | * 6/1988 | ............... F16P 3/12 |
| RU | 2365102 C2 | 8/2009 | |

OTHER PUBLICATIONS

International Search Report and Written Opinion dated Apr. 28, 2016 for PCT/US2015/058254.

*Primary Examiner* — James Choi
(74) *Attorney, Agent, or Firm* — Kilpatrick Townsend & Stockton LLP

(57) ABSTRACT

Provided is a decontamination apparatus and method involving a base, and a plurality of sources that each emit UVC light to render a target object pathogen reduced. A plurality of adjustable supports couple the sources to the base, and a controller is coupled to the base to be operatively connected to the sources to control emission of the UVC light. A housing is removably installed on the base to protect the plurality of sources. A remote control is provided to the housing and includes a user interface that receives a input from a user and transmits a control instruction to the controller based on the input received, resulting in desired operation of the sources by the controller.

20 Claims, 9 Drawing Sheets

(56) References Cited

U.S. PATENT DOCUMENTS

| | | |
|---|---|---|
| 7,721,383 B2 | 5/2010 | Garcia |
| 7,819,910 B2 | 10/2010 | Fiset |
| 7,921,853 B2 | 4/2011 | Fiset |
| 7,923,707 B2 | 4/2011 | Garcia |
| 7,994,489 B2 | 8/2011 | Fiset |
| 8,067,750 B2 | 11/2011 | Deal |
| 8,105,532 B2 | 1/2012 | Harmon |
| 8,186,004 B2 | 5/2012 | Garcia |
| 8,226,887 B2 | 7/2012 | Harmon |
| 8,330,121 B2 | 12/2012 | Douglas |
| 8,455,832 B2 | 6/2013 | Statham |
| 8,662,705 B2 | 3/2014 | Roberts |
| 8,680,496 B2 | 3/2014 | Leben |
| 8,682,576 B2 | 3/2014 | Kurtti |
| 8,791,441 B1 | 7/2014 | Lichtblau |
| 8,816,301 B2 | 8/2014 | Stibich |
| 8,841,634 B2 | 9/2014 | Statham |
| 8,859,994 B2 | 11/2014 | Deal |
| 9,095,633 B1 | 8/2015 | Dayton |
| 2003/0216795 A1 | 11/2003 | Harth |
| 2004/0175290 A1 | 9/2004 | Scheir |
| 2004/0249369 A1 | 12/2004 | Muzzi et al. |
| 2008/0065175 A1 | 3/2008 | Russell et al. |
| 2009/0143842 A1 | 6/2009 | Cumbie |
| 2009/0191100 A1* | 7/2009 | Deal ................. A61L 2/10 422/105 |
| 2010/0032589 A1 | 2/2010 | Leben |
| 2010/0104471 A1 | 4/2010 | Harmon |
| 2011/0243789 A1 | 10/2011 | Roberts |
| 2011/0256019 A1 | 10/2011 | Gruen et al. |
| 2012/0076702 A1* | 3/2012 | Dunkley ........... A61L 2/202 422/186.12 |
| 2012/0093688 A1 | 4/2012 | Harmon |
| 2012/0121457 A1* | 5/2012 | Farren ............... A61L 2/10 422/3 |
| 2012/0243789 A1 | 9/2012 | Yang |
| 2012/0282135 A1 | 11/2012 | Trapani |
| 2013/0002445 A1 | 1/2013 | Stibich |
| 2013/0234041 A1 | 9/2013 | Deal |
| 2013/0243647 A1 | 9/2013 | Garner |
| 2013/0280126 A1 | 11/2013 | Statham |
| 2014/0044590 A1 | 2/2014 | Trapani |
| 2014/0212332 A1 | 7/2014 | Bergman |
| 2014/0227132 A1 | 8/2014 | Neister |
| 2014/0330452 A1* | 11/2014 | Stewart ............ B25J 11/0085 701/2 |
| 2015/0086420 A1* | 3/2015 | Trapani ............ A61L 2/202 422/24 |
| 2015/0204701 A1* | 7/2015 | Klicpera ........... G01M 3/00 137/624.11 |

\* cited by examiner

DECONTAMINATION SYSTEM AND DECONTAMINATION UNIT HOUSING EQUIPPED WITH REMOTE CONTROL

BACKGROUND OF THE INVENTION

1. Field of the Invention

This application relates generally to a method and apparatus for decontaminating an enclosed space and, more specifically, to a remote-controllable decontamination apparatus and a method of remotely controlling a decontamination apparatus to avoid exposing a person with a decontaminating agent.

2. Description of Related Art

Conventional decontamination devices include an ultraviolet light source that broadcasts ultraviolet light towards all exposed surfaces in a room to be decontaminated. Such an apparatus is positioned at a desired location within the room and an "on" button is pushed to turn the ultraviolet light source on. A delay circuit can be provided to the decontamination device to provide the operator sufficient time to exit the room after pushing the on button to avoid exposing the operator to the ultraviolet light emitted.

As an extra precaution, a sign can be placed in front of the door leading into the room instructing people not to enter the room while the decontamination device is active. Further, a remote control can be used by the operator to activate the decontamination device from outside of that room, once the operator has exited the room. But utilizing all of these precautionary measures requires a remote control, a warning sign, etc. to be transported as separate items from location to location to decontaminate different rooms, which is inconvenient to the operator. Further, it is likely that one or more of such objects will be lost as the decontamination device is repeatedly transported and deployed.

BRIEF SUMMARY OF THE INVENTION

According to one aspect, the subject application involves decontamination apparatus including a base and a plurality of sources that each emit UVC light at a suitable intensity to at least partially decontaminate a target object on which the UVC light is imparted to render the target object pathogen reduced. A plurality of adjustable supports couple the sources to the base. Each of the adjustable supports includes an adjustment mechanism that is to be manipulated to adjust a position of one of the sources relative to the base. A controller coupled to the base is operatively connected to the sources to control emission of the UVC light. A housing is to be removably installed on the base to protect the plurality of sources while installed on the base, and a remote control is provided to the housing. The remote control includes a user interface that receives an input from a user and a housing transmitter that transmits a control instruction to the controller based on the input received at the user interface from a location remote from the base to result in desired operation of the sources.

According to another aspect, the subject application involves a method of decontaminating a target object within a room and minimizing exposure of an occupant of the room to UVC light. The method includes supporting, relative to a base, a plurality of sources that each emit UVC light at a suitable distance from the target object to at least partially decontaminate the target object with the UVC light emitted. A communication channel is established between a controller operatively connected to the sources to control emission of the UVC light and a remote control that is provided to a housing to be installed on the base to protect the sources against direct impacts. The controller receives a control instruction transmitted by the remote control provided to the housing from a remote location relative to the base, outside of the room. The control instruction is indicative of user input entered at a user interface of the remote control. The sources are then activated according to the control instruction.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
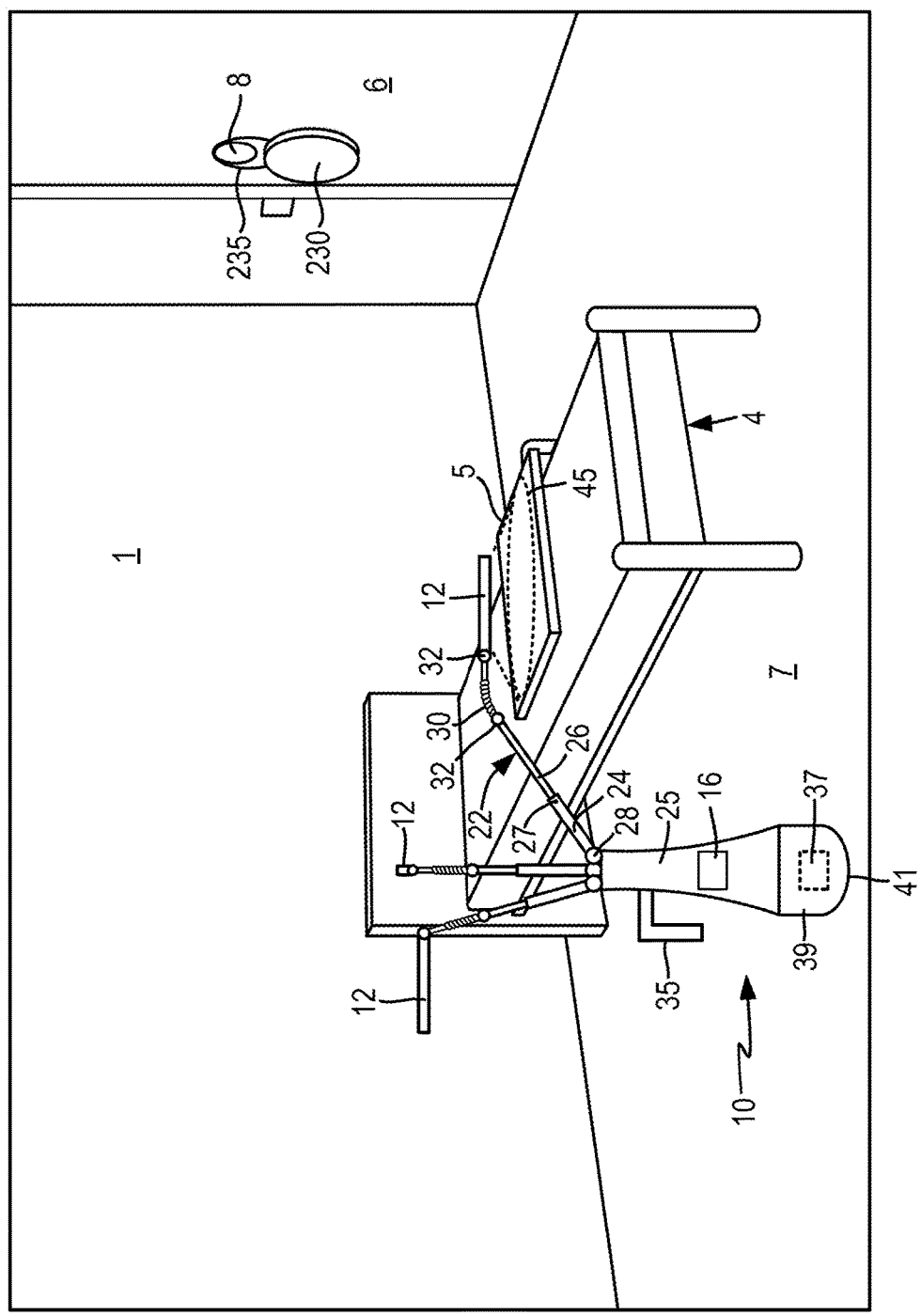
FIG. 1 shows a schematic representation of a decontamination system installed in an inpatient hospital room.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

FIG. 1 shows an illustrative embodiment of an inpatient room 1 in a hospital that is accessible through a door 6 separating the inpatient room from a hallway, for example. The room 1 is provided with a patient bed 4 and a tray table 5 that can extend over the patient lying in the bed 4. Although not shown, the room 1 can also include other fixtures and features commonly found in inpatient rooms such as a television, remote control, health-monitoring equipment such as a heart-rate monitor, telephone, nightstand, etc. Further, although the present disclosure focuses on the decontamination of items within an inpatient hospital room 1 for the sake of clarity and brevity, the technology disclosed herein can be used to decontaminate objects located anywhere, such as in hotel rooms any other public accommodations.

Also disposed within the room 1 shown in FIG. 1 is a decontamination apparatus 10 operable to at least partially decontaminate, or at least render pathogen reduced, contaminated surfaces such as the tray table 5 within that room 1. The decontamination process can be initiated manually, and performed by the decontamination apparatus 10 on demand, and/or can optionally be initiated automatically according to a predetermined schedule when the room 1 is unoccupied, as determined utilizing a plurality of sensors as described below.

Rendering the surfaces "pathogen reduced" with the decontamination apparatus 10 does not necessarily require the subject surfaces to be 100% sterile, free of any and all living organisms that can viably reproduce. Instead, to be considered pathogen reduced, there must be a lower level of living contagions on the decontaminated surfaces capable of reproducing or otherwise causing an infection after performance of the decontamination process than the level that existed on the surfaces prior to performance of the decontamination process. For example, the exposed surfaces in the bathroom can be considered to be pathogen reduced if at least a 1 $\log_{10}$ reduction of such contagions on the surfaces remain infectious (i.e., no more than 1/10th of the biologically-active contagions originally on the exposed surfaces remain active or infectious at a time when the decontamination process is completed) occurs. According to yet other embodiments, the surfaces can be considered pathogen reduced once at least a 3 $\log_{10}$ reduction (i.e., 1/1,000th) of such contagions on the surfaces is achieved.

Generally, the decontamination apparatus 10 includes one or a plurality of sources 12 that direct a decontaminating agent toward the surface(s) to be rendered pathogen reduced, a redundant occupant sensing system that determines whether the room 1 is occupied or not, and a controller 16 that interferes with emission of the decontaminating agent by the source(s) 12 if the room 1 is, or becomes occupied based on a signal from the occupant sensing system. Each source 12 can be any apparatus that emits a decontaminating agent that, when exposed to the surfaces, renders those exposed surfaces pathogen reduced. For the illustrative embodiments described herein and shown in the drawings, each source 12 includes an ultraviolet light source that is to be energized to emit UVC light as the decontaminating agent, and the surface to be rendered pathogen reduced is described as the tray table 5.

As shown, each source 12 includes at least one, and optionally a plurality of UVC bulbs 14 (FIG. 2) supported adjacent to a reflective surface 18 coupled to an underside of a shade 20. The shade 20 and/or source 12 itself can be pivotally coupled to a distal end of an articulated arm 22 or other suitable support that allows the shade 20, and accordingly the bulbs 14, to be pivoted about a rotational axis in the directions indicated by arrow 21 (FIG. 3) and otherwise positioned in a suitable position relative to the tray table 5 to achieve the desired level of decontamination within a predetermined period of time, once activated. The bulbs 14 can be of limited available power, and/or the controller 16 can be configured to operate the bulbs 14 to emit UVC light at an intensity that is insufficient to render the target object 5 pathogen reduced in less than 10 minutes while the sources are separated from the target object by a distance greater than eighteen (18) inches.

Figure 3:
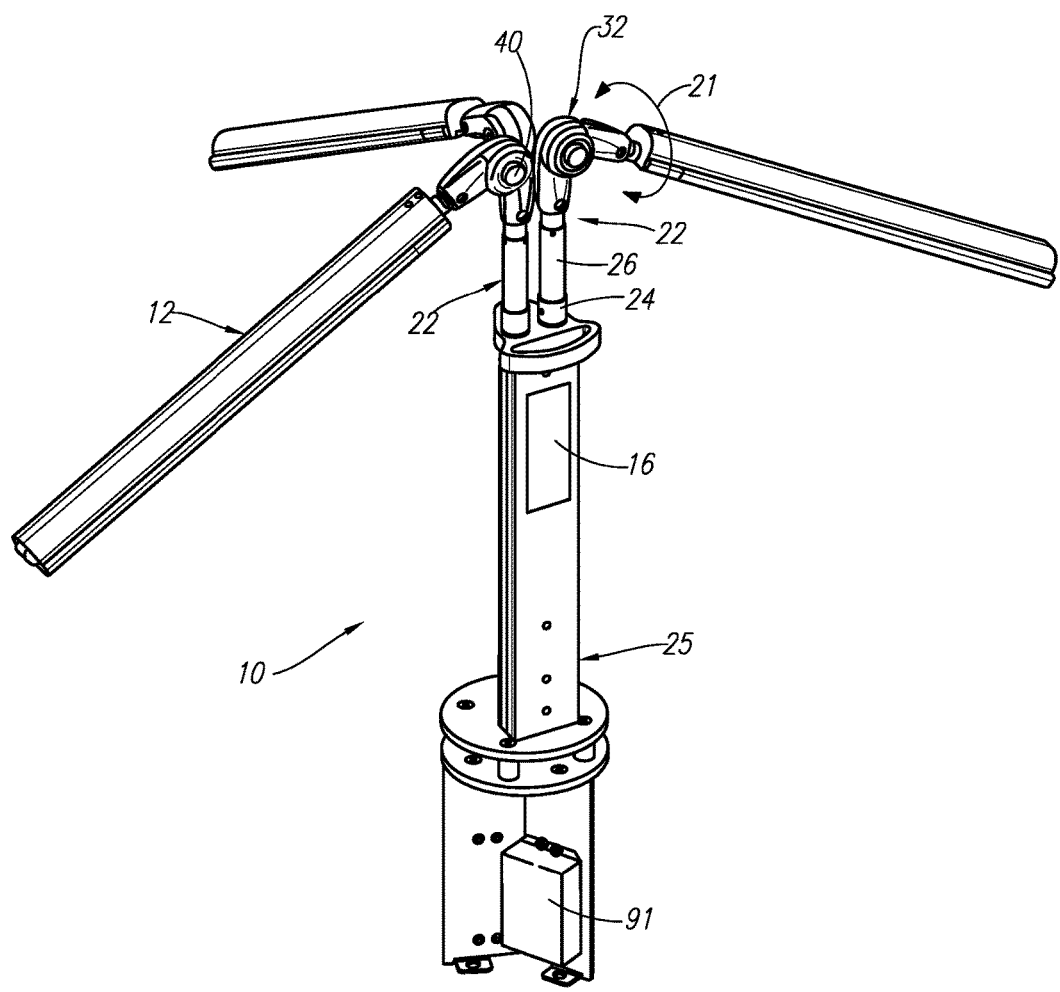
FIG. 3 is a perspective view of a decontamination apparatus with a plurality of sources in a deployed state and a lower cap of a base removed.

According to the embodiments in FIGS. 1 and 3, each arm 22 has a segment with an adjustable length extending generally away from a base portion 25, which can be facilitated by an external member 24 that telescopically receives an internal member 26, or other suitable length adjustment mechanism (e.g., sliding track, etc.). A locking member 27 such as a spring-biased pin urged toward a locking position, a friction fit between the internal and external members 24, 26, etc. can be provided to one or more the of the adjustable length portions to maintain a desired length of the arm 22, once manually established. A hinge 28 or other connector suitable to allow angular adjustment of the arm 22 relative to the base 25 can optionally be disposed between the base 25 and the arm 22. A bendable joint 30 can optionally also be provided anywhere along the length of the arm 22, such as adjacent to the distal end of the arm 22 where the shade 20 is supported. The joint 30 can be formed from a plastically-deformable flexible material that can be manually bent to position the shade 20, yet be sufficiently rigid to maintain the position of the housing relative to the arm 22 once the bending force has been removed. Further, one or a plurality of hinges 32 can also optionally be positioned along the arm 22 before and/or after the joint 30 to allow further adjustment of the position of the shade 20 and bulbs to achieve the desired coverage of the tray table 5 with UVC light. As with any of the hinges described herein, the hinge(s) 32 can be selectively lockable, meaning a locking member such as a set screw, for example, can be loosened to allow the structures coupled to opposite sides of the hinge(s) 32 to be pivotally adjusted relative to each other. Once the desired adjustment has been completed, the set screw or other locking member can be tightened to interfere with further pivotal adjustment of the structures relative to each other. According to an alternate embodiment such as that shown in FIG. 3, the hinge 32 can optionally be adjusted through selective actuation of a push button 40 that, when pressed, allows for free adjustment of the hinge but maintains the relative position of the adjusted portions once the button 40 is released.

Figure 4:
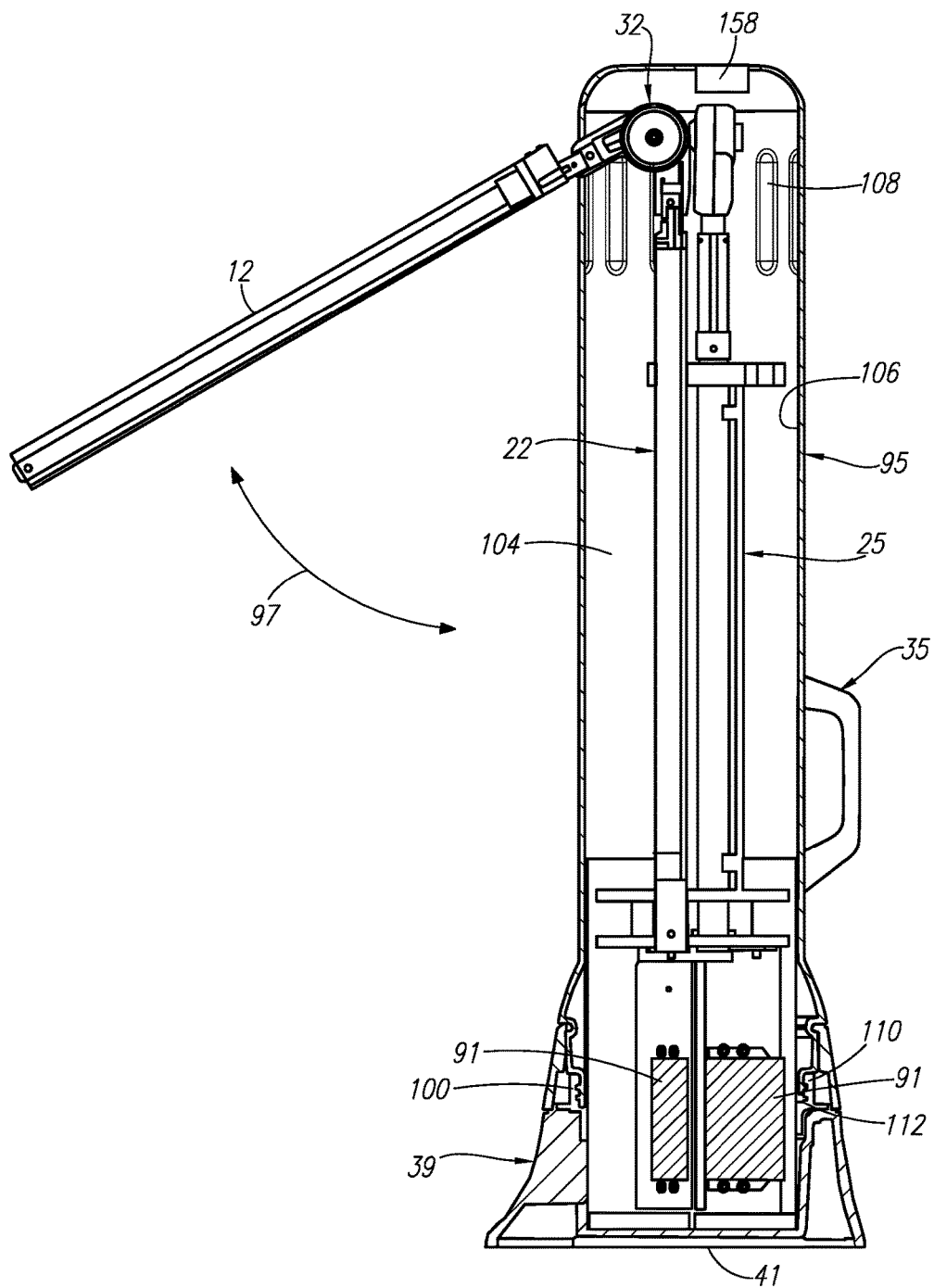
FIG. 4 is a partially cutaway view of a decontamination apparatus illustrating an arrangement of a housing that encloses a plurality of sources in a stowed state.

The base 25 supports the arms 22 at a desired elevation above the floor 7 of the room 1. The base 25 supports the controller 16 that can be manipulated by a user to control operation of the decontamination apparatus 10 (e.g., independently control operation of each source 12 to emit UVC light, optionally to cause one source 12 to remain energized longer than another one of the sources 12, or collectively control a plurality, or all of the sources 12 to operation in a similar and coordinated manner), and optionally houses an on-board power supply such as a rechargeable lithium ion or other suitable battery bank 37 storing electric energy that can be used to energize the bulbs 14 and power the controller 16. Being relatively heavy, the battery bank 37 can be housed within a recess defined by a lower cap 39 of the base 25. The lower cap 39 can optionally include an arcuate bottom surface 41 that rests on the floor 7, or can include a bottom surface 41 with a larger footprint than elsewhere along the lower cap 39 (e.g., greater lateral dimensions at the bottom surface 41 than at another elevation vertically above the bottom surface 41) as shown in FIG. 4. The arcuate bottom surface 41 allows the decontamination apparatus 10 to wobble, if necessary, to properly position the bulbs 14 for a decontamination process. The large footprint bottom surface 41 shown in FIG. 4 provides the base with a stable, stationary platform that allows a plurality, and optionally all of the arms 22 to be fully extended in the same radial direction outward, away from the base 25 without tipping over. The base 25, or another portion of the decontamination apparatus 10 can optionally be provided with an accelerometer, tip sensor, gyroscope or other type of monitoring device that can sense when the decontamination apparatus 10 has been picked up, falls over, moved or otherwise disturbed. In such events, an active decontamination process can be terminated and a new decontamination process can be prevented from being initiated. For the embodiment shown in FIG. 4, the lighting ballast 91, which regulates the current through the UVC bulbs 14. The lower cap 39 can be threadedly connected to the base 25 so as to be removable (e.g., repeatedly removed and reconnected without damaging the lower cap 39), and optionally interchangeable. For removable embodiments, the lower cap 39 can be unscrewed from the base 25 to grant access to the battery bank 37, the ballasts 91, or other components hidden by the lower cap 39 when installed on the base 25. In this manner, a depleted battery bank 37 can then be removed from the decontamination apparatus 10 and replaced with a charged battery bank 37. For embodiments where the battery bank 37 is integrated into the lower cap 39, the lower cap with the depleted battery bank 37 can be replaced in its entirety with another lower cap 39 with a charged battery bank 37. According to alternate embodiments, the decontamination apparatus can include a power cord that is to be plugged into an AC mains electric outlet supplied by an electric power utility to obtain the electric energy needed to power the decontamination apparatus 10.

Figure 5:
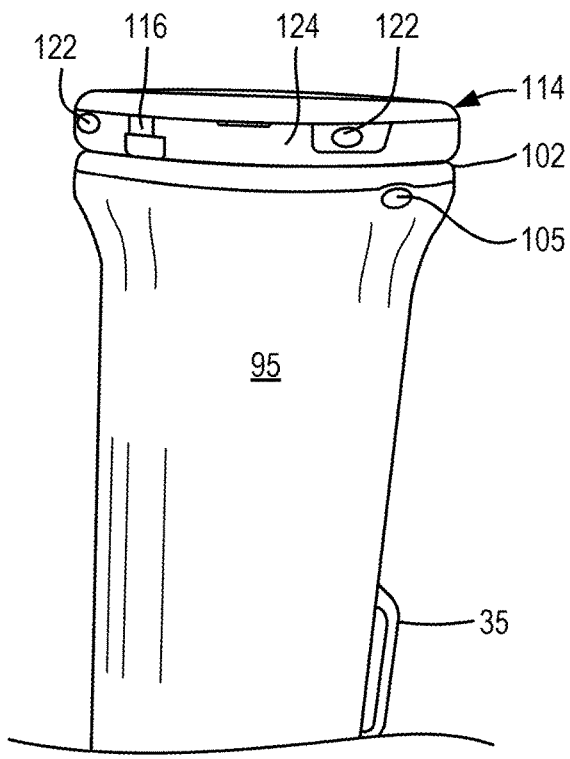
FIG. 5 is a perspective view of a housing provided with a satellite monitoring unit removably coupled to a protective housing of a decontamination apparatus.

The base 25 can also optionally be provided with a connector, shown in FIG. 1 as a hook 35 that is generally shaped to resemble an upside-down "L". The hook 35 can be placed over a receiver or other portion of a cart hauling cleaning supplies, for example, or any other transport vehicle, to allow transportation of the decontamination apparatus 10 throughout the hospital for use in a plurality of different rooms 1. According to alternate embodiments, the hook 35 can be formed as an enclosed handle that extends radially outwardly, away from an exterior periphery of a protective housing 95, as shown in FIGS. 4 and 5. The housing 95 can be installed over the sources 12 that have been pivoted about the hinge 32 in the counterclockwise direction indicated by arrow 97 in FIG. 4 into a stowed state (e.g., vertically oriented adjacent to the base 25). The sources 12 can be pivoted about the hinge 32 in the opposite, clockwise direction indicated by arrow 97 to be returned to the deployed state.

Figure 2:
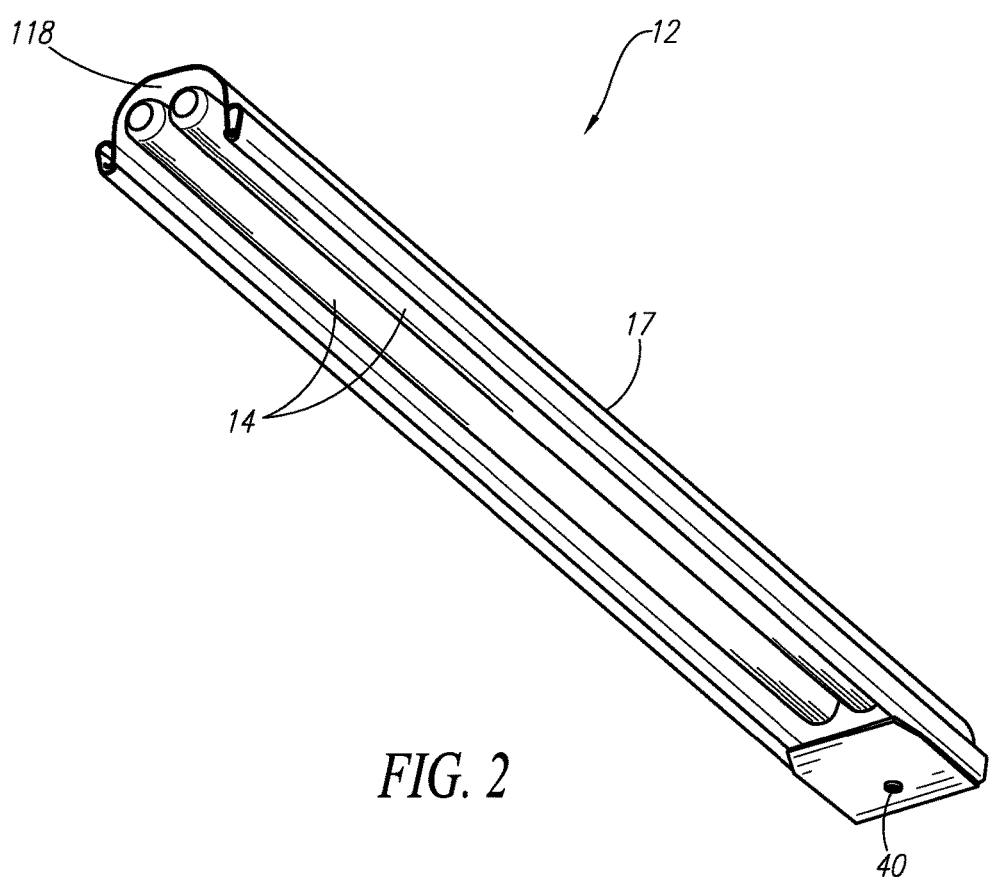
FIG. 2 is a bottom, perspective view of a source of a decontaminating agent in the form of UVC light, the source being provided adjacent to a terminal end of an articulated arm and being viewed from the perspective indicated by arrow 2 in FIG. 1.

To help with adjustment of the shade 20 and/or reflective shield 18, a focal indicator 40 can optionally be provided to the reflective shield 18 and/or shade 20. Locating the focal indicator 40 between the UVC bulbs 14 as shown in FIG. 2 allows the focal indicator to identify a general direction that is representative of the direction in which the UVC light from the UVC bulbs 14 will be focused. The focal indicator 40 can include a light emitting diode ("LED"), laser light, or other optical indicator that can project light that will illuminate a region of a surface on which the UVC light from the UVC bulbs 14 is centered. An example of such a region is illustrated in FIG. 1 by the broken lines 45 appearing on the tray table 5. Thus, a user can essentially aim the UVC light toward the surfaces to be rendered pathogen reduced, and get a sense of the portion of the tray table 5 that will be suitably exposed to the UVC light during a decontamination apparatus to be considered pathogen reduced within a predetermined period of time for the power of the bulbs 14 employed.

As shown in FIG. 4, the decontamination apparatus 10 includes a cap, or housing 95 that is installed on the base 25 to circumferentially enclose the sources 12 in the stowed state. According to the illustrative embodiment shown, the housing 95 is formed as a cylindrical shell that extends between a fastener end 100 and a top portion 102, defining a cylindrical interior passage 104 there between. The bulbs 14 are stowed within the interior passage 104 and protected against damage from external impacts by the housing 95 installed on the decontamination apparatus 10. The housing 95 can be molded from a plastic material that is sufficiently durable to resist impacts without deforming to an extent that causes an interior surface 106 of the housing 95 to contact, and thereby damage the sources 12. According to alternate embodiments, the housing 95 can be formed from a metallic material by stamping, roll forming, welding, riveting or otherwise fixing the metallic material into the desired, cylindrical shape. Vents 108 can optionally be formed in the housing 95 to allow the housing 95 to be installed onto the base 25 even while the bulbs 14 remain at an elevated temperature following the performance of a decontamination process as described herein. The vents 108 can be sized to interfere with the introduction of large objects into the interior passage 104, and can optionally be formed at a height corresponding to an elevation of the hinges 32 or other objects that are not as fragile as the glass UVC bulbs 14 while the sources 12 are in the stowed state.

The fastener end 100 of the housing 95 can optionally include external threading 110 that cooperates with internal threading 112 provided to the lower cap 39 or other portion of the base 25, for example. Causing the threading 110 of the housing 95 to engage the threading 112 of the lower cap 39 by rotating the housing 95 clockwise when viewed from above the top portion 102, for example, couples the housing 95 to the base 25 with sufficient retention to allow the decontamination apparatus 10, as a whole, to be lifted and transported when grasped by the handle 35. The handle 35 can also optionally be positioned at a balanced location along the longitudinal axis of the housing 95 to enable the decontamination apparatus 10 to be substantially horizontal (e.g., ±15° from horizontal) while being transported by the handle 35.

Although external threading 110 provided to the housing 95 is described as mating with internal threading 112 provided to the lower cap 39, the fastening system for securely installing the housing 95 onto the decontamination apparatus is not so limited. Any adjustable fastening system and/or device that allows the housing 95 to be removably installed (e.g., repeatedly coupled to, released from and re-coupled to the base 25 without rendering the fastening system inoperable or otherwise damaging the fastening system) on the base 25 can be utilized. For example, releasable latches, threaded mechanical fasteners and the like can be used in place of the threading described in detail herein.

Figure 7:
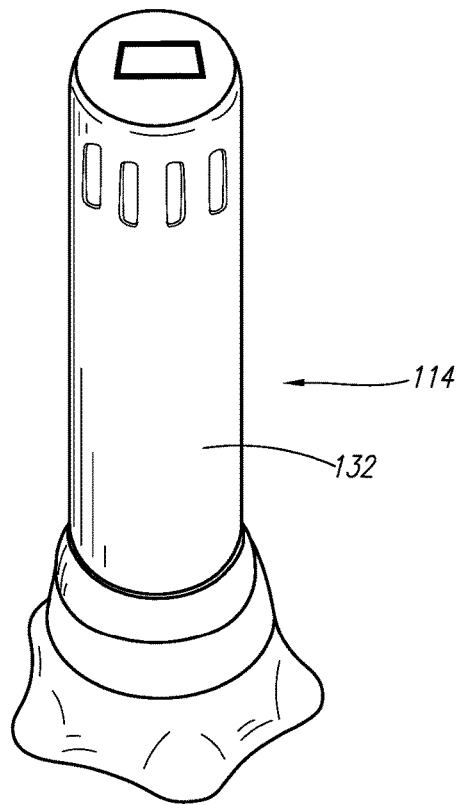
FIG. 7 is a perspective view of an alternate embodiment of a satellite monitoring unit with an upright form factor.
Figure 9:
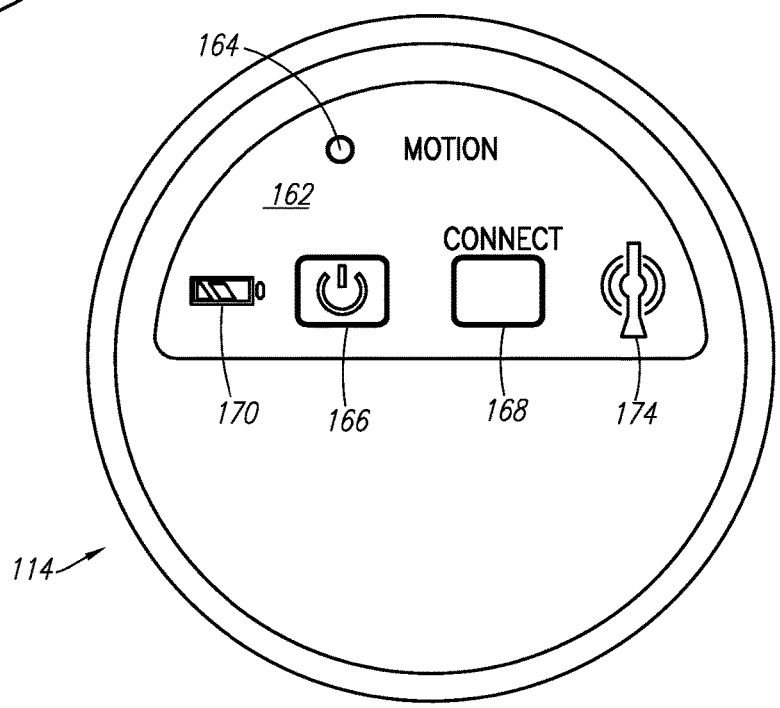
FIG. 9 shows an illustrative embodiment of a user interface of satellite monitoring unit that can detect a condition that has been deemed to require deactivation of sources provided to a decontamination apparatus.
Figure 8A:
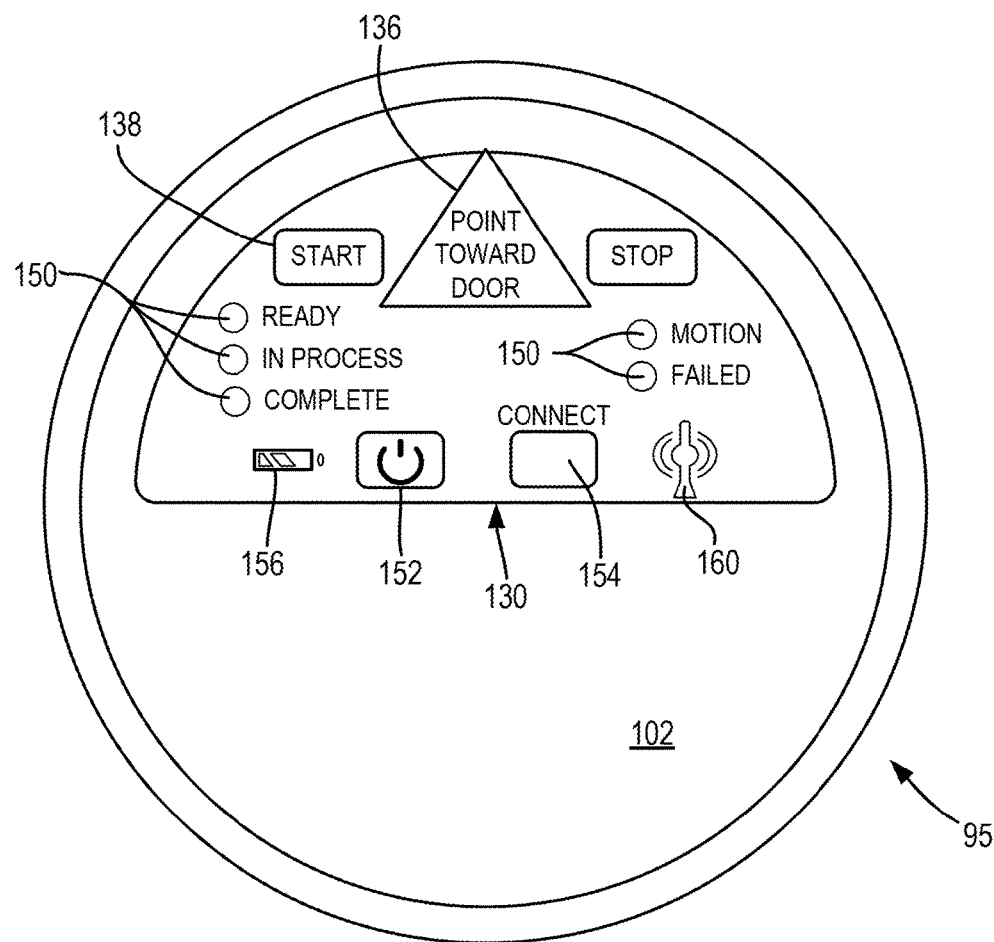
FIG. 8A shows an illustrative embodiment of a user interface forming a portion of a remote control provided to a housing that is to be installed on a decontamination apparatus to protect a plurality of sources against direct impacts.
Figure 8B:
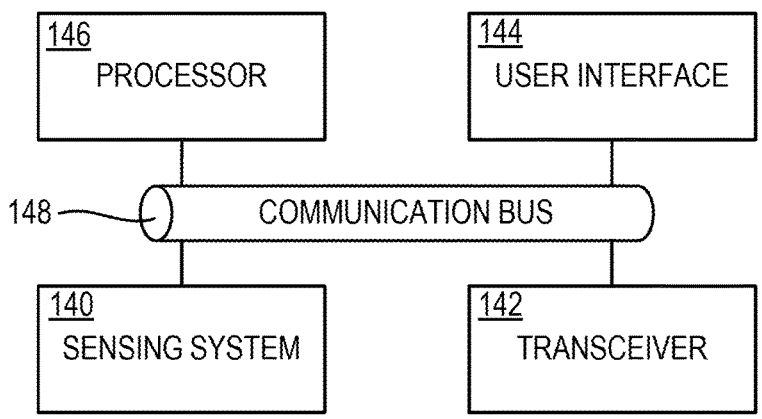
FIG. 8B is a block diagram schematically illustrating electronic components that collectively form the operational aspects of at least one of a controller provided to a base, a remote control provided to a housing, and/or a monitoring system provided to a satellite monitoring unit.

The controller 16 provided to the base 25 (FIG. 3), a remote control 130 (FIG. 8A) coupled to (or integrally formed as part of, and not removable from) the housing 95, and a monitoring system of a satellite monitoring unit 114 (FIGS. 5-9) can each include at least a portion of the operational components schematically depicted in the block diagram of FIG. 8B. A sensing system 140 includes a single sensor, or a plurality of sensors that are each operable to sense a condition deemed to require deactivation of the sources 12, and transmits an interruption signal in response to sensing such a condition. The sensing system 140 can optionally include, in addition to or in lieu of the aforementioned sensor(s), an accelerometer that senses changes in the acceleration of the controller 16, the housing 95 and/or the monitoring unit 114 to detect a disruption to those devices (e.g., the housing 95 is bumped, jostled, picked up, etc., indicating that someone is attempting to walk around the housing 95 positioned outside of the door 6 as described below to enter the room 1). The condition(s) sensed by the sensing system 140 provided to the controller 16, the housing 95 and/or the monitoring unit 114 can be the same, or different. But each condition sensed can be generally indicative of an attempt to enter the room 1 (FIG. 1) in which the sources 12 are emitting UVC light, and/or the presence of an occupant within the room while the sources 12 are emitting UVC light.

The interruption signal is communicated to a processor component 146 via a communication bus 148 to be interpreted so the processor component 146 can determine the condition sensed, and the portion of the sensing system 140 that sensed the condition. The processor component 146 transmits a signal via the communication bus 148 to cause a user interface 144 to provide a proper indication of the condition sensed by the sensing system 140. The indication can be a visible indication (e.g., illumination of a LED), an audible indication (e.g., an alarm broadcast by a speaker), or a combination thereof. Depending on the location of the sensing system 140 that detected the condition, a transceiver 142 including at least a transmitter and/or a receiver can optionally transmit a wireless signal (e.g., Bluetooth, IEEE 802.11, other short-range communication protocol, etc.) that is received by the controller 16, which is operatively connected to the sources 12 to control the emission of the UVC light. The controller 16, in turn, deactivates the sources 12.

The operational components discussed generally above will now be described in detail with respect to the controller 16, the housing 95 and the satellite monitoring unit 114.

Housing Remote Control

The top portion 102 of the housing 95, when installed on the base 25, extends over top of the arms 22 while the sources 12 are in their stowed state. Adjacent to the top portion 102 is/are arranged one, and optionally a plurality of sensors 105 included as part of the remote control 130. Each sensor 105 is arranged on the housing 95 and aimed to monitor a region extending radially away from the external periphery of the housing 95, when standing upright, with the fastener end 110 resting on the floor. The sensor(s) 105 is/are operable to sense a condition deemed to require deactivation of the sources 12, and transmit an interruption signal in response to sensing such a condition to notify the controller 16 of such a condition, resulting in deactivation of the sources 12. Examples of the sensor(s) 105 include, but are not limited to: a motion detector that senses a change in the proximity of an object (e.g., the exterior surface of the door 6) relative to the sensor 105, motion of a human or other living being in front of the sensor 105 (e.g., between the sensor 105 and the external surface of the door 6), and the like. The sensors(s) 105 can utilize any suitable technology to detect the conditions indicative of entry into the room 1 where the sources 12 are emitting UVC light, such as an optical signal (e.g., infrared), a microwave signal, and/or an acoustic signal (e.g., radio frequency) to sense movement of the door 6 or the presence of an object between the door 6 and the sensor 105. The sensing system 140 of the housing 95 can optionally include, in addition to or in lieu of the sensor(s) 105, an accelerometer that senses changes in the acceleration of the housing 95 (e.g., the housing 95 is bumped, jostled, picked up, etc.).

An embodiment of the housing 95 includes a single sensor 105 (or a plurality of commonly aimed sensors 105 focusing on the same target region) to render the housing 95 a unidirectional monitoring system, monitoring a single region extending radially outward away from that sensor 105. Such embodiments of the housing 95 can be placed in front of, and outside of the door 6 leading into the room 1 in which the sources 12 are to emit UVC light during a decontamination process as described in detail below. The sole sensor 105 can be aimed directly at the door 6 to sense the opening of the door 6, but not sensing other movement such as pedestrians walking down the hallway past the door 6, but behind the housing 95 placed in front of the door 6. As described in detail below, a transmitter portion of a transceiver system 142 provided to the housing 95 can transmit the interruption signal that will be received by a receiver provided to the controller 16 which, in turn, deactivates the sources 12.

An illustrative embodiment of the user interface 134 provided to the remote control 130 of the housing is supported on the top portion 102 in FIG. 8A. As shown, the user interface 134 includes a reference point 136 identifying the direction of the region to be monitored by the sensor 105. The apex of the triangular reference point 136 in FIG. 8A points in the direction of the monitored region. A start button 138 is provided to receive a user instruction to begin a decontamination process during which the bulbs 14 are to be energized. In response to the start button 138 being pressed, a transmitter provided to the transceiver portion of the remote control 130 transmits an instruction to commence the decontamination process to be received by a receiver provided to the transceiver portion of the controller 16. In response to receiving this instruction, the controller 16 activates the sources 12 and the bulbs 14 emit UVC light.

A status section includes a plurality of visible indicators 150 that can be selectively activated to provide a status update regarding the progress of a decontamination process. These indicators can inform the operator when the decontamination apparatus is ready to perform a decontamination process, when a decontamination process is underway, and when a decontamination process has progressed to completion without any unscheduled interruptions. In the event a decontamination process is prematurely interrupted, unexpectedly as the result of the sensor 105 sensing a predetermined condition (e.g., motion of the door 6), the motion indicator 150 will be illuminated. If the fault that prematurely terminated the decontamination process was sensed by a sensor other than the sensor 105 provided to the housing 95, the "failed" indicator can be illuminated, alerting the operator that the problem causing premature termination of the decontamination process originated elsewhere.

The user interface 134 also includes a power button 152 that can be selected to turn the remote control 130 provided to the housing 95 on/off, and a connect button 154 that is selectable to specifically pair the remote control 130 of the housing 95 to the controller 16 provided to the base 25 within the room 1. A battery indicator 156 conveys an indication of the remaining life of a battery 158 supplying electric energy to power the remote control 130, while a network indicator 160 indicates whether the remote control 130 has been specifically paired with the controller 16.

Specifically pairing the remote control 130 (or other device) with the controller 16 means that the effect of signals transmitted by the transceiver component of the remote control 130 (or other device) will be limited to that controller 16. In other words, a signal transmitted by the remote control 130 to the controller 16 with which it is specifically paired will cause the controller 16 to perform an action consistent with the transmitted signal. However, even if another, different controller to which the remote control 130 is not paired is within range of the remote control 130, that different controller will not respond to the signal transmitted by the remote control 130. Accordingly, many remote controls paired to different controllers can be used within close proximity to each other without unintended interference.

Figure 11:
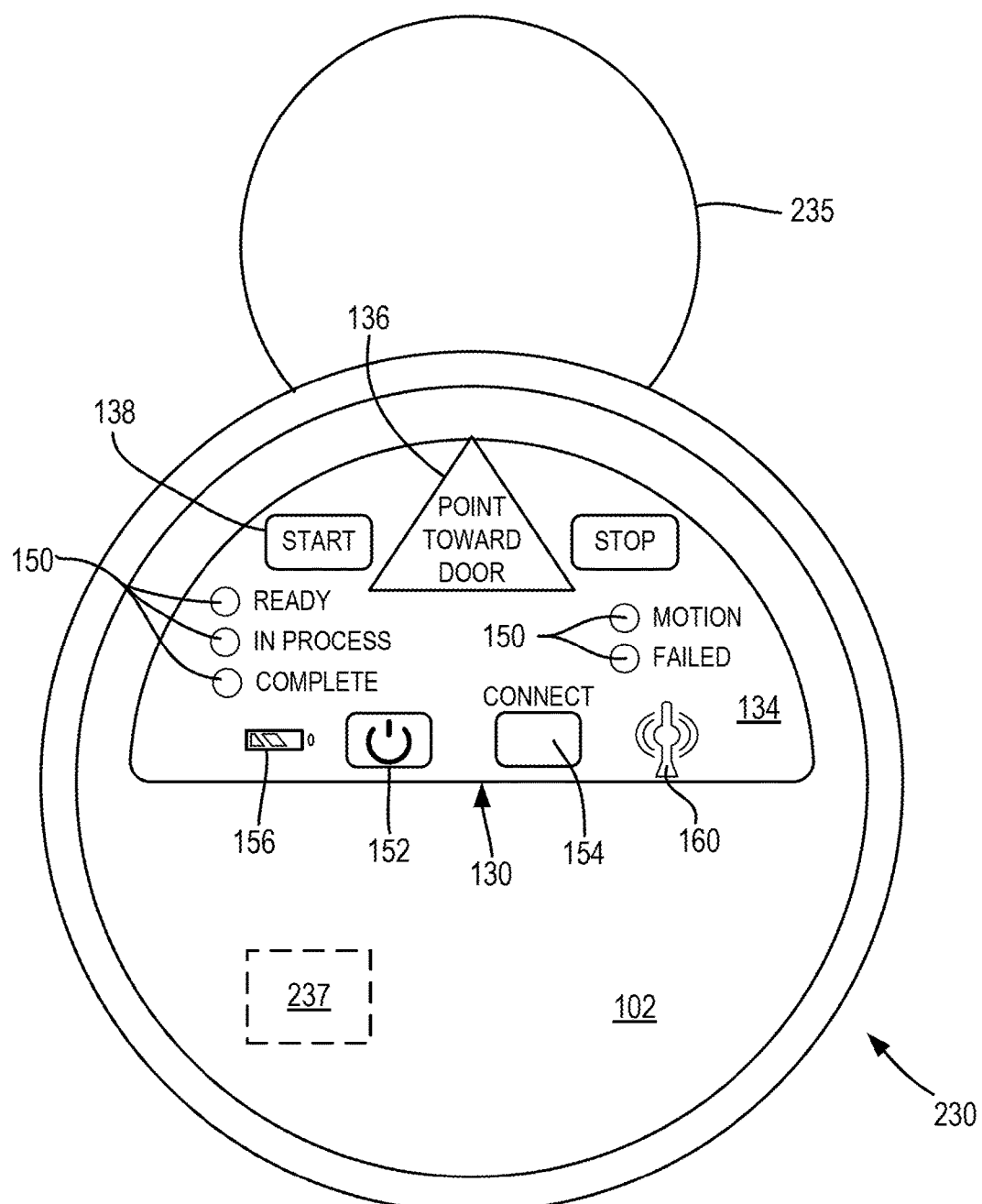
FIG. 11 shows a top view of an alternate embodiment of a remote control.

According to an alternate embodiment, the elongated cylindrical housing 95 can optionally be omitted from the decontamination apparatus 10. For such an embodiment, the sources 12 can be adjusted to a stowed position as shown in FIG. 3, but left exposed while being transported. Since the housing 95 is omitted, the remote control 130 is also omitted, replaced in function by a separate, stand-alone remote control 230 (FIG. 11) having the same, or similar form factor as the monitoring unit 114 described below with respect to FIGS. 5 and 6. A top view of such a remote control 230 is shown in FIG. 11. As shown, the remote control 230 includes the same control features provided to the user interface 134 of the remote control 130 described above, and optionally also the same sensors 122 described above.

Being compact enough to be held in the hand of the user, the remote control 230 can also include a hangar 235 that protrudes away from the housing of the remote control 230 to allow the remote control 230 to be hung or otherwise supported on an object in the room 1. Although shown as a flexible loop of material, the hangar 235 can be formed as a hook, a single strap, or be configured in any other shape suitable to be hung from a door handle 8 as shown in FIG. 1, for example. As shown in FIG. 11, the remote control 230 also includes an accelerometer 237 in place of, or in addition to the optional sensors 122. When suspended from the door handle 8, the remote control 230 remains stationary until the door 6 is opened or otherwise disturbed. Such disturbances tend to cause movement of the remote control 230, which is detected by the accelerometer 237 and/or sensors 122. Thus, attempts to gain access to the interior of the room 1 while the decontamination apparatus 10 is operational can be detected and a decontamination process interrupted.

Satellite Monitoring Unit

As shown in FIG. 5, the top portion 102 of the housing removably supports a satellite monitoring unit 114 that is operable to sense a condition deemed to require deactivation of the sources 12, and transmit an interruption signal in response to sensing such a condition to notify the controller 16 of such a condition, resulting in deactivation of the sources 12. Again, the removable nature of the support afforded the monitoring unit 114 allows the monitoring unit 114 to be repeatedly removed from the housing 95 and subsequently re-coupled to the housing 95 without damaging the housing 95 or the monitoring unit 114. Thus, damage to an extent that interferes with the cooperation between the monitoring unit 114 and the housing 95 that prevents the monitoring unit 114 from being transported on the housing 95 can be avoided. To remove the monitoring unit 114 from the top portion 102, an operator can manually press or pull one or more release levers 116, shown in FIGS. 5 and 6, to cause separation of cooperating mechanical fasteners provided to the monitoring unit 114 and/or the housing 95, allowing the monitoring unit 114 to be lifted off of the housing 95.

Figure 6:
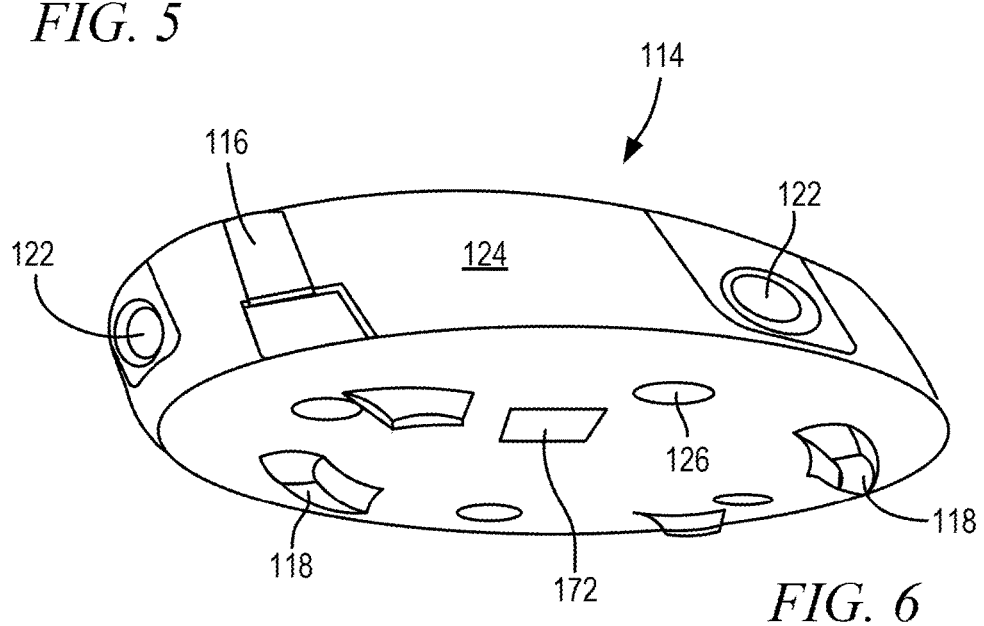
FIG. 6 shows a perspective view of the satellite monitoring unit in FIG. 5 separated from the housing.

The embodiment of the monitoring unit 114 shown in FIGS. 5 and 6, the monitoring unit 114 has a low-profile, creating the appearance that the monitoring unit 114 forms a cap resting on top of the housing 95. The bottom 120 of the monitoring unit 114, removed from the housing in FIG. 6, includes a plurality of feet 118 formed from a rubber or other vibration absorbing material that protrude downwardly from the bottom surface 120. The feet 118, and/or optional bosses extending upwardly from the top portion 102 can cooperate with a compatible apertures 126 formed in the housing 95 and/or monitoring unit 114, respectively, to enhance the relative stability of those components when coupled together.

An alternate embodiment of the monitoring unit 114 having an upright form factor is shown in FIG. 7. According to the present embodiment, the monitoring unit includes a cylindrical housing 132 with a shape and dimensions approximately equal to those of the housing 95. The cylindrical housing 132 can optionally define an internal passage with internal dimensions that are slightly larger than the internal dimensions of the housing 95, allowing the cylindrical housing 132 of the monitoring unit 114 to be placed over the housing 95 of the decontamination apparatus. Unlike the embodiment of the monitoring unit 114 shown in FIGS. 5 and 6, however, the cylindrical housing 132 can rest on the floor and support sensors such as the sensors 122 described below at an elevation (e.g., at least 18 inches, or at least 24 inches, etc.) above the floor. However, for the sake or brevity, the sensors 122 and operation of the monitoring unit 114 will be described with reference to the embodiment of the monitoring unit 114 shown in FIGS. 5 and 6.

One, or a plurality of sensors 122 forming a portion of the sensing system 140 provided to the monitoring unit 114 can be arranged about a portion of the lateral periphery 124 of the monitoring unit 114 to monitor conditions in one or more directions (optionally 360° about the monitoring unit 114) extending radially outward from the monitoring unit 114. Examples of the one or plurality of sensors 122 include, but are not limited to motion sensors that utilize one or more of an optical (e.g., infrared), microwave, or acoustic (e.g., radio frequency) signal to sense movement within the room 1. The sensing system 140 of the monitoring unit 114 can optionally include, in addition to or in lieu of the sensor(s) 122, an accelerometer that senses changes in the acceleration of the monitoring unit 114 (e.g., the monitoring unit 114 is bumped, jostled, picked up, etc.). Thus, examples of conditions sensed by the monitoring unit 114 include, but are not limited to the presence of a human occupant within the room in which the sources 12 are emitting UVC light, a disruption to the monitoring unit 114 itself (e.g., the monitoring unit 114 is jarred or knocked over, an object falls on the monitoring unit 114, etc.), and the like.

Similar to the remote control 130 provided to the housing 95, the transceiver 142 of the monitoring unit 114 includes a transmitter that transmits a signal indicative of the sensed condition to the controller 16, thereby resulting in a deactivation of the bulbs 14. According to one embodiment, the monitor unit 114 can optionally not be paired specifically to the controller 16 provided to the base 25 of the decontamination apparatus 10. Instead, the transmitter provided to the transceiver 142 of the monitoring unit 114 can optionally broadcast the interruption signal that results in deactivation of sources 12 to be received by any and all controllers provided to bases within a transmission range of the monitoring unit 14. For such embodiments, the monitor unit 114 transmitter emits an alternating signal having a frequency outside of a range from about 20 Hz to about 20 kHz, which is perceptible to the human ear, and the controller 16 includes a receiver configured to listens and detect this alternating signal as the interruption signal. Thus, one monitoring unit 114 can cause deactivation of the bulbs 14 provided to a plurality of different bases. According to alternate embodiments, however, the monitoring unit 114 can optionally be paired specifically with the controller 16 provided to the base 25, to limit the effect of an interruption signal to that specific base 25.

The monitoring unit 114 also includes a user interface 162 to receive user input and convey information about the status of a decontamination process and/or the state of the monitoring unit 114. For example, the user interface includes a visible indicator 164 (e.g., LED) to indicate that one or more sensors 122 of the monitoring unit 114 detected movement, which caused premature termination of the decontamination process. The user interface 162 also includes a power button 166 that can be selected to turn the monitoring unit 114 on/off, and a connect button 168 that is selectable to specifically pair the monitoring unit 114 to the controller 16 provided to the base 25 within the room 1. A battery indicator 170 conveys an indication of the remaining life of a battery 172 supplying electric energy to power the monitoring unit 114, while a network indicator 174 indicates whether the remote control 130 has been specifically paired with the controller 16.

Base Controller

Figure 10:
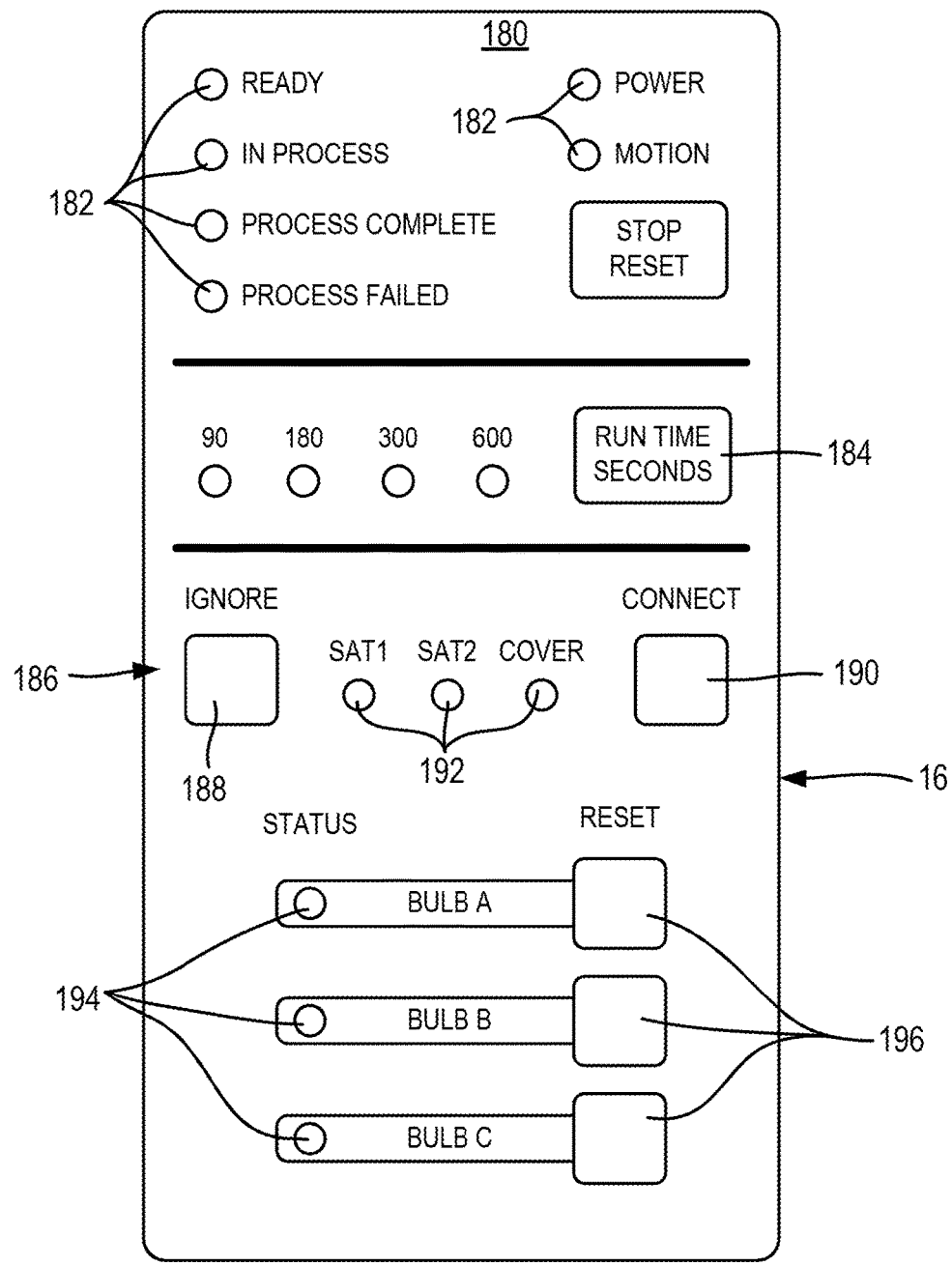
FIG. 10 shows an illustrative embodiment of a controller supported by a base of a decontamination apparatus and operatively connected to a plurality of sources to control the delivery of a decontaminating agent.

The controller 16 provided to the base (FIG. 3) is operatively connected to the sources 12 to control the emission of the UVC light by the bulbs 14 in response to signals received by the transceiver 142 of the controller 16. The user interface 180 (FIG. 10) of the controller 16 includes a status section with a plurality of visible indicators 182 that can each be selectively activated to provide a status update regarding the progress of a decontamination process. These indicators can inform the operator when the decontamination apparatus 10 is ready to perform a decontamination process, when a decontamination process is underway, and when a decontamination process has progressed to completion without any unscheduled interruptions. In the event a decontamination process is prematurely interrupted unexpectedly, as the result of a sensor provided to the base 25 sensing a predetermined condition (e.g., motion within the room 1), as described in U.S. patent application Ser. No. 14/530,510 to Dayton, which is hereby incorporated in its entirety by reference, the motion indicator 182 will be illuminated. If the fault that prematurely terminated the decontamination process was sensed by a sensor other than the sensor provided to the base 25, the "process failed" indicator 182 can be illuminated, alerting the operator that the problem causing premature termination of the decontamination process originated elsewhere.

A runtime selection button 184 is selectable by an operator to establish the desired runtime of the decontamination process during which the sources 12 will remain active, and the bulbs 14 will emit UVC light. Each press of the runtime selection button 184 cycles to the next available, preprogrammed runtime option. According to the embodiment illustrated in FIG. 10, there are four available runtime options: 90 seconds, 180 seconds, 300seconds and 600 seconds.

The user interface 180 also includes a connection section 186 that is operable to control the remote devices that are paired specifically to the controller 16. Visible indicators 192 such as LEDs can be illuminated by the processor 146 of the controller 146 to identify the remote device that has transmitted a pair request. When a remote device is identified through activation of one of the indicators an ignore button 188 can be selected to disregard the pair request from that remote device. If a connection is desired, a connect button 190 can be selected to establish the wireless communication channel over which the paired remote device will transmit an interruption signal to be received by the controller 16 to deactivate the sources 12.

The user interface 180 also includes indicators 194 (e.g., LEDs) that identify one or more bulbs 14 that have experienced an unexpected or undesirable operational state. For example, if Bulb A is not activated in response to an instruction from the remote control 130 to commence a decontamination process, the indicator 194 corresponding to Bulb A can be illuminated to inform the operator that Bulb A did not function properly, and may require replacement. Since the bulbs 14 can be independently controlled and operated at different times and for different durations, Bulb A may exceed its recommended useful life before Bulb B, for example. Again, the indicator 194 corresponding to Bulb A can be illuminated to alert the operator of this condition. Once the condition giving rise to the activation of one or more indicators 194 has been addressed, the reset button 196 can be actuated to input a clearance command to the processor 142 of the controller 16, clearing the error and resetting the status of the respective bulb 14.

In use, an operator can transport the decontamination apparatus 10 to a desired location with one or more target surfaces to be rendered pathogen reduced by carrying the decontamination apparatus 10 by the handle 35. The base 25 can be placed adjacent to the target surfaces and the housing 95 removed, thereby granting the user access to the sources 12 and the controller 16. The arms 22 are adjusted to position the sources 12, and particularly the bulbs 14, within a predetermined effective distance from the target surfaces to achieve the desired level of pathogen reduction within a predetermine runtime. The base 25 is then plugged into an AC mains wall outlet, or otherwise turned on for battery-operated embodiments, to energize the controller 16.

The remote control 130 (FIG. 8A) of the housing 95 can optionally be paired to the controller 16 at the time of manufacturing. However, if the controller 16 has been reset or is otherwise not paired specifically with the remote control 130 of the cover 95 in which it was housed, the remote control 130 is to be paired specifically with the controller 16 before the decontamination process can be activated using the user interface 134 of the remote control 130. To establish the communication channel between the remote control 130 and the controller 16, the remote control 130 is powered on through selection of the power button 152, and the pairing process is begun by selection of the connect button 150 of the remote control. In response, the transmitter of the remote control 130 transmits a pair request that is received and recognized by the controller 16, causing the "cover" indicator 192 to flash or otherwise indicate that the remote control 130 of the housing 95 is being paired. Since it is desired to establish this communication channel, the connect button 190 (FIG. 10) included in the user interface 180 of the controller 16 is pressed to pair the remote control 130 with the controller 16. The cover indicator 192 is then constantly illuminated or otherwise used to indicate that pairing was successful. Likewise, the network indicator 160 (FIG. 8A) of the remote control's user interface 134 is illuminated to indicate that pairing was a success.

Similarly, if a satellite monitoring unit 114 is to be used it can be paired with the controller 16 is a similar manner. The monitoring unit 114 can be powered on by pressing the power button 166 (FIG. 9), and then the connect button 168 can be pressed to begin the pairing process to establish the wireless communication channel between the monitoring unit 114 and the controller 16. The transceiver 142 of the monitoring unit 114 transmits a request to pair, and this transmission is received and recognized by the controller 16, causing the "sat1" indicator 192 to flash or otherwise indicate that the monitoring unit 114 is being paired. Since it is desired to establish this communication channel, the connect button 190 (FIG. 10) included in the user interface 180 of the controller 16 is pressed to pair the monitoring unit 114 with the controller 16. The sat1 indicator 192 is then constantly illuminated or otherwise used to indicate that pairing was successful. Likewise, the network indicator 174 (FIG. 9) of the monitoring unit's user interface 162 is illuminated to indicate that pairing was a success. A second or additional monitoring units can optionally also be paired and used during a decontamination cycle.

With pairing complete, the monitoring unit 114 can be placed anywhere within the effective communication range of the monitoring unit 114 and the controller 16 for the wireless communication channel established, inside or outside of the room 1 where the base 25 is located. For example, the monitoring unit 114 can be placed within the room 1, at a location approximately 5 feet in front of a secondary door leading into the room 1. At such a location, the sensors 122 of the monitoring unit 114 can monitor the state of the secondary door and sense if that door is opened during emission of the UVC light.

The housing 95 is to be placed immediately (e.g., within 12 inches) outside of the primary door 6 leading into the room 1 in which the base 25 is located. The housing 95 is to be positioned outside of the door 6 with the reference point 136 (FIG. 8A) pointing at the exterior surface of the door 6 to ensure the sensor 105 (FIG. 5) is arranged to detect when the door 6 is adjusted from a closed state, or when a person enters the space between the sensor 105 and the door 6, but not sense movement or other conditions that occur outside of the region where the sensor 105 is focused. Thus, the hallway outside the door 6 remains usable, while the sensor 105 ensures nobody enters the room 1 while the bulbs 14 are emitting UVC light.

Once the monitoring unit 114 and the housing 95 are properly positioned, the operator selects the desired runtime of the decontamination process by pressing the runtime selection button (FIG. 10) on the controller 16 the appropriate number of times to select the desired runtime. After the desired runtime has been entered, the operator can exit the room 1 and press the start button 138 (FIG. 8A) provided to the user interface 134 of the remote control 130, causing the transceiver 142 of the remote control 130 to transmit an instruction to commence the decontamination process for the desired runtime. In response to receiving the signal transmitted by the remote control 130, the controller 16 activates the sources 12, thereby causing the bulbs 14 to emit UVC light.

Throughout the decontamination process the sensors 122 of the monitoring unit 114 and the sensor 105 of the housing 95 continuously monitor their respective regions of concern. If neither the monitoring unit sensors 122 nor the housing sensor 105 detects a condition deemed to require premature termination of the decontamination process, the process remains active for the entire runtime and the complete indicator 150 (FIG. 8A) of the user interface 134 on the housing 95 and the process complete indicator 182 (FIG. 10) on the controller 16 indicate that the decontamination process was not interrupted, and was successfully completed.

If, however, the a sensor provided to the monitoring unit 114 and/or the housing 95 and/or the controller 16 senses one of conditions warranted interruption of the decontamination process, the respective transceiver 142 transmits the interrupt signal, which is received by a receiver provided to the transceiver 142 of the controller. In response, the controller 16 terminates the decontamination process by deactivating the bulbs 14, ceasing UVC light emission. The transceiver 142 of the controller 16 transmits a notification signal, causing the appropriate visible indicator provided to the user interface of the monitoring unit 114 and/or the remote control 130 to be activated, thus alerting the operator to the premature termination of the decontamination process and the location of the fault.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A decontamination apparatus comprising:
 a base;
 a plurality of sources that each emit UVC light at a suitable intensity to at least partially decontaminate a target object on which the UVC light is imparted to render the target object pathogen reduced;
 a plurality of adjustable supports coupling the sources to the base, wherein each of the adjustable supports is adjustable relative to another one of the adjustable supports to independently position the plurality of sources for emitting the UVC light in different directions, and comprises an adjustment mechanism that is to be manipulated to move the sources coupled to the adjustable supports relative to the base between: (i) a stowed state, and (ii) a deployed state in which the sources emit the UVC light to render the target object pathogen reduced;
 a controller that is coupled to the base and operatively connected to the sources to control emission of the UVC light;
 a housing comprising a protective shell that defines an interior space in which the sources, in the stowed state, are received while the housing is removably installed on the base, wherein the protective shell of the housing extends about the plurality of sources, and protects the plurality of sources in the stowed state against direct impacts while the housing is installed on the base; and a remote control supported by the housing so the remote control is removable from the base as a portion of the housing, wherein the remote control comprises a user interface that receives an input from a user and a housing transmitter that transmits a control instruction to the controller based on the input received at the user interface from a location remote from the base to result in desired operation of the sources.

2. The decontamination apparatus of claim 1, wherein the suitable intensity of the UVC light emitted by the sources is insufficient to render the target object pathogen reduced in less than ten (10) minutes while the sources are separated from the target object by a distance greater than eighteen (18) inches.

3. The decontamination apparatus of claim 1, wherein the housing transmitter of the remote control is paired specifically with the controller to limit an effect of the control instruction to the decontamination apparatus.

4. The decontamination apparatus of claim 3 further comprising a monitoring unit that is to be positioned independently of the base, wherein the monitoring unit comprises a sensor that detects a condition deemed to require deactivation of the sources, and a monitor transmitter configured to transmit an interruption signal that is received by the controller and results in deactivation of the sources.

5. The decontamination apparatus of claim 4, wherein the sensor comprises an accelerometer and/or a motion sensor.

6. The decontamination apparatus of claim 4, wherein the monitor transmitter is not paired specifically to the decontamination apparatus, and broadcasts the interruption signal to result in deactivation of sources provided to at least a second decontamination apparatus within a transmission range of the monitoring unit.

7. The decontamination apparatus of claim 6, wherein the monitor transmitter emits an alternating signal having a frequency outside of a range from about 20 Hz to about 20 kHz, and the controller comprises a listening device adapted to detect the alternating signal.

8. The decontamination apparatus of claim 4, wherein the monitoring unit comprises an upright form factor with a shape that is approximately the same as a shape of the housing.

9. The decontamination apparatus of claim 4, wherein the monitoring unit comprises a compact form factor and a releasable fastener portion that cooperates with a compatible portion of the housing to removably couple the monitoring unit from the housing.

10. The decontamination apparatus of claim 4, wherein the monitor transmitter is paired specifically with the controller of the decontamination apparatus to limit an effect of the interruption signal to the decontamination apparatus, and to avoid interfering with operation of another decontamination apparatus that is not paired with the monitoring unit, but is within a transmission range of the monitor transmitter.

11. The decontamination apparatus of claim 1, wherein the housing comprises a housing sensor that detects a condition deemed to require deactivation of the sources, and the housing transmitter is configured to transmit an interruption signal that is to be received by the controller and cause deactivation of the sources.

12. The decontamination apparatus of claim 11, wherein the housing sensor comprises an accelerometer and/or a motion sensor.

13. A method of decontaminating a target object within a room and minimizing exposure of an occupant of the room to UVC light, the method comprising:

independently supporting, relative to a base, a plurality of sources that each emit UVC light at separate positions that are each a suitable distance from the target object to at least partially decontaminate the target object with the UVC light emitted;

establishing a communication channel between: (i) a controller operatively connected to the sources to control emission of the UVC light, and (ii) a remote control that is supported by a housing to be installed on the base, wherein the housing comprises a protective shell that extends about the plurality of sources while the housing is installed on the base, and the plurality of sources in a stowed state are received in an interior space defined by the protective shell, to protect the plurality of sources against direct impacts while the plurality of sources are in the stowed state;

with the controller, receiving a control instruction transmitted by the remote control supported by the housing, the housing supporting the remote control at a remote location relative to the base, outside of the room, wherein the control instruction is indicative of user input entered at a user interface of the remote control at the remote location; and activating the sources according to the control instruction.

14. The method of claim 13 further comprising:
establishing a runtime during which the sources are to remain operational; and
in response to expiration of the runtime, deactivating the sources.

15. The method of claim 13, wherein said activating the sources according to the control instruction comprises establishing a suitable intensity of the UVC light emitted by the sources insufficient to render the target object pathogen reduced in less than ten (10) minutes while the sources are separated from the target object by a distance greater than eighteen (18) inches.

16. The method of claim 13, wherein said receiving the control instruction comprises receiving a wireless signal indicative of the control instruction from the remote control over a wireless communication channel established between the remote control and the controller by specifically pairing the remote control with the controller to limit an effect of the control instruction to the decontamination apparatus to which the remote control is paired.

17. The method of claim 13 further comprising:
receiving an interruption signal transmitted from a housing transmitter provided to the housing indicating a condition deemed to require deactivation of the sources exists; and
deactivating the sources in response to said receiving the interruption signal.

18. The method of claim 17, wherein the interruption signal indicates that a sensor provided to the housing has sensed movement indicative of occupant entering the room in which the sources are emitting UVC light, and/or an acceleration of the housing at a remote location outside of the room.

19. The method of claim 17 further comprising:
establishing a second communication channel with a monitoring unit that is to be positioned independently of the base and the housing, wherein the controller is to receive an interruption signal transmitted by the monitoring unit via the second communication channel in response to the monitoring unit sensing a condition indicative of an occupant within the room.

20. The method of claim 19, wherein the interruption signal transmitted by the monitoring unit indicates that a sensor provided to the monitoring unit sensed movement indicative of occupant entering the room in which the sources are emitting UVC light, and/or an acceleration of the monitoring unit at a remote location relative to the base.

* * * * *